United States Patent
Kennaway (12)

(10) Patent No.: US 6,403,651 B1
(45) Date of Patent: Jun. 11, 2002

(54) MEDIATION OF CIRCADIAN RHYTHMS

(75) Inventor: David Kennaway, South Australia (AU)

(73) Assignee: Luminis Pty Limited, South Australia (AU)

(*) Notice: Subject to any disclaimer, the term of this patent is extended or adjusted under 35 U.S.C. 154(b) by 0 days.

(21) Appl. No.: 09/402,024

(22) PCT Filed: Mar. 26, 1998

(86) PCT No.: PCT/AU98/00207
§ 371 (c)(1),
(2), (4) Date: Mar. 6, 2000

(87) PCT Pub. No.: WO98/42331
PCT Pub. Date: Oct. 1, 1998

(30) Foreign Application Priority Data

Mar. 26, 1997 (AU) ............................................. PO 5882

(51) Int. Cl.$^7$ ...................... A61K 31/135; A61K 31/55; A61K 31/50; A61K 31/495; A61K 31/44
(52) U.S. Cl. .................. 514/654; 514/214.02; 514/220; 514/254.06; 514/255.03; 514/288
(58) Field of Search ............................ 514/654, 255.03, 514/254.06, 214.02, 220, 288

(56) References Cited

U.S. PATENT DOCUMENTS

| 4,902,691 A | 2/1990 | Cohen et al. |
| 5,278,160 A | 1/1994 | Abou-Gharbia et al. |

FOREIGN PATENT DOCUMENTS

| EP | 0246910 | 11/1987 |
| WO | WO 95/05819 | 3/1995 |
| WO | WO 97/31629 | 9/1997 |
| WO | WO 97/39001 | 10/1997 |

OTHER PUBLICATIONS

Neuropharmacology, vol. 33 No. 3/4, Mar.–Apr. 1994 pp. 467–471, "Slow Wave Sleep in Humans: Role of 5–HT$_{2a}$ and 5–HT$_{2c}$ Receptors", Sharpley et al.
J. Pharm. And Pharmacol. vol. 31, 1979 pp. 246–248, "The effect of neuroleptic drugs on serum and cerebrospinal fluid melatonin concentration in psychiatric subjects", Smith et al.
Biol. Psych. vol. 37, 1995, pp. 740–749, "Hermonal Response to the administration of mChlorophenylpiperazine in Patients with seasonal affective disorder and controls", Garcia–Borreguero et al.
Neuropsychopharmacology, vol. 13 No. 2, 1995, "Serotonin and Thermoregulation", Schwartz et al.
Postgraduate Medicine, vol. 86 No. 5 Oct. 1989 "Seasonal affective disorder: Shedding light on a dark subject", Chung et al.
Trends in Pharmac. Sciences, vol. 14, Jun. 1993, pp. 233–236, "A proposed new nomenclature for 5–HT receptors", Humphrey et al.
J. Clin. Endo. and Metab., vol. 61, No. 6, 1985 "Neuroendocrine Effects of mChlorophenylpiperazine, a serotonin agonist", Mueller et al in part Fig. 1 and Fig. 3.
Australian Pharmac. Publish. Co., pp. 1348, 2050, 800, 974, 668, 1850, published 1995.
Martindale, The Extra Pharmacopoeia, 30th Ed. 1993, Pharm. Press pp. 272, 602, 589, 842.
The Merck Index, 15 Ed., 1996, Mon. No: 6527, 8399, 5307, 6217, 3703, 5541, 5999, 6222.

Primary Examiner—William R. A. Jarvis
(74) Attorney, Agent, or Firm—Marshall, Gerstein & Borun (57) ABSTRACT

Method for mediating the effects of light on melatonin rhythmicity in mammals and a method of mediating circadian rhythms, effected by the administration of a compound or compounds effective at a 5-HT2c serotonin receptor site. By administration of selected doses of the 5-HT2c receptor active compound it is possible to advance or delay circadian rhythms as measured by the rate of melatonin production or moderation of core body temperature rhythms.

12 Claims, 9 Drawing Sheets

| Drug | Dose | Receptor | Delay on Night 3 | Delay on Night 4 | Fos positive cells |
|---|---|---|---|---|---|
| DOI | 5 mg/kg | 5-HT2a/2c | 2.2 ± 0.2* | 2.3 ± 0.15* | 193 ± 27* |
| DOI | 0.5 mg/kg | 5-HT2a/2c | 1.7 ± 0.2* | 2.1 ± 0.2* | 95 ± 35* |
| DOI | 0.1 mg/kg | 5-HT2a/2c | 1.2 ± 0.2* | 2.3 ± 0.2* | 41 ± 12* |
| mCPP | 2 mg/kg | 5-HT2a/2c | 1.7 ± 0.3* | 1.7 ± 0.4* | 11 ± 4* |
| TFMPP | 2 mg/kg | 5-HT2a/2c | 1.4 ± 0.8* | 1.5 ± 0.4* | 5 ± 3 |
| MK-212 | 2 mg/kg | 5-HT2a/2c | 0.7 ± 0.3 | 0.3 ± 0.7 | NA |
| Buspirone | 2 mg/kg | 5-HT1a | 0.2 ± 0.2 | 0.5 ± 0.5 | 7 ± 5 |
| Phenylbiguanide | 10 mg/kg | 5-HT3 | 0.0 ± 0.2 | 0.3 ± 0.4 | NA |
| R-(+)-8-OH-DPAT (a) | 2 mg/kg | 5-HT7 | -0.1 ± 0.1 | 0.5 ± 0.1 | NA |
| Quipazine (b) | 1 mg/kg | 5-HT2c (?) | 0.8 ± 0.1* | 1.5 ± 0.5* | NA |
| Quipazine (b) | 3 mg/kg | 5-HT2c (?) | 1.3 ± 0.3* | 2.1 ± 0.3* | NA |
| (±)-8-OH-DPAT (b) | 5 mg/kg | 5-HT1a | 0.5 ± 0.2 | 0.9 ± 0.3 | NA |
| Saline | | | 0.3 ± 0.2 | 0.4 ± 0.2 | 3 ± 2 |

| Antagonist | Dose of antagonist | DOI | Fos positive cells |
|---|---|---|---|
| Ritanserin | 1.4 μmole/kg | 1.4 μmole/kg | 26 ± 5 |
| Ritanserin | 0.7 μmole/kg | 1.4 μmole/kg | 38 ± 19 |
| Ritanserin | 0.14 μmole/kg | 1.4 μmole/kg | 157 ± 41 |
| Ritanserin | 6.3 μmole/kg | 0 | 33 ± 5 |
| Ketanserin | 1.4 μmole/kg | 1.4 μmole/kg | 51 ± 13 |
| Ketanserin | 0.7 μmole/kg | 1.4 μmole/kg | 95 ± 25* |
| Ketanserin | 0.14 μmole/kg | 1.4 μmole/kg | 109 ± 25 |
| Ketanserin | 18 μmole/kg | 0 | 14 ± 3.3 |
| None | 0 | 1.4 μmole/kg | 141 ± 23 |

FIG. 7

| Antagonist | Dose | Light | Delay to Night 3 | Delay to Night 4 | Fos positive cells |
|---|---|---|---|---|---|
| Metergoline | 15 mg/kg | 2 lux/ 1 min | 2.8 ± 0.5* | 2.7 ± 0.6* | 182 ± 41* |
| Ritanserin | 3 mg/kg | 2 lux/ 1 min | 2.0 ± 0.4* | 2.5 ± 0.5* | 106 ± 19* |
| LY 53,857 | 3 mg/kg | 2 lux/ 1 min | 2.0 ± 0.3* | 2.2 ± 0.5* | NA |
| None | 0 | 2 lux/ 1 min | 2.6 ± 0.2* | 3.1 ± 0.2* | 149 ± 18* |

MEDIATION OF CIRCADIAN RHYTHMS

This application is a 371 of PCT/AU98/00207, filed Mar. 26, 1998.

FIELD OF THE INVENTION

The present invention relates to a method of mediating the effects of light on melatonin rhythmicity and, accordingly a method of mediation of circadian rhythms. The invention further relates to a method of treatment of conditions associated with dysfunctional or arrhythmic melatonin production.

BACKGROUND OF THE INVENTION

Daily, or circadian, rhythms are common to all eukaryotic biological organisms, including humans. Circadian rhythms help coordinate a number of functions, most notably sleeping patterns.

There is a growing awareness for the human population of the involvement of circadian rhythms, and consequent state of sleepfulness or wakefulness, on human health, safety and productivity. It is recognised that physical and mental abnormalities associated with night work or shift work and rapid travel across time zones involve disruptions of the human circadian clock system and the sleep-wake cycle controlled by it. Other health problems associated with a disrupted circadian rhythm include insomnia, some forms of depression, and Seasonal Affective Disorder (SAD). The ability to manipulate circadian rhythms is therefore desirable and offers benefits to those industries with a need for shift work, to long distance travellers and to other sufferers from the various illnesses associated with disrupted circadian rhythms.

In addition, circadian rhythms are of importance in the control of seasonal breeding cycles of a number of economically important animals such as horses, sheep, deer and goats. A greater control of these breeding seasons provides breeders with increased flexibility and the potential for increased productivity and/or profit.

It is now well established that the hormone melatonin plays a crucial role in the maintenance of circadian rhythms. Melatonin is known to be produced in the pineal gland only during hours of sleep/darkness, the production ceasing with daybreak. The cycle of melatonin production and the cessation of production therefore underlie the circadian rhythm and because of this, crude attempts to control or alter the rhythm by administering melatonin have been made.

It is further known that the area of the hypothalamus known as the suprachiasmatic nucleus (SCN) coordinates, amongst other rhythmic physiological processes, the production of melatonin in the pineal gland. It is thus the endogenous rhythmicity of the SCN, modulated in time by retinally perceived light, that is responsible for the precise timing of the melatonin rhythm. The neural pathways of the SCN are a key factor in the control of pineal melatonin production.

The current understanding is that there are three pathways by which light influences SCN function, and thus ultimately melatonin secretion. The first is the retino-hypothalamic tract which utilises neurons originating in retinal ganglion cells and projecting to the ventro-lateral SCN area. The second pathway is an indirect multi-synaptic pathway which involves retinal ganglion cell projections to the intergeniculate leaflet and then via neurones returning to the SCN. A third, more controversial projection involves a retinal-raphe nucleus pathway which incorporates a raphe-SCN projection. Whereas the first two projections are known to exist in both hamsters and rats, the latter pathway has not been found in hamsters.

The retino-hypothalamic tract appears to use excitatory amino acids (EEAs; eg, aspartate, glutamate) as the major neurotransmitters, and it has been suggested that EEAs might mediate the effects of light at the level of the SCN. However, experiments conducted by the present inventor lead to the conclusion that EEAs are not involved in mediating the effects of light on the SCN of rats, or that an alternative pathway exists in parallel with the retino-hypothalamic tract.

Further investigations made by the present inventor have followed from the notion that serotonergic pathways may be involved in circadian rhythmicity, and the present invention is predicated on the discovery that a serotonergic pathway utilising 5-HT2c receptor in the SCN is involved in mediating the effects of light on melatonin rhythmicity.

SUMMARY

Therefore, according to one aspect of the present invention, there is provided a method of mediating the effects of light on melatonin rhythmicity or mediating the effects of cicadian rhythms in mammals in need of such treatment comprising administering a therapeutically effective amount of a compound, or compounds, having a high affinity for a serotonin 5-HT2c receptor.

Advantageously, the timing of administration of the compound can be predetermined to coincide with an appropriate phase on an existing circadian rhythm to produce a selected mediation of the cycle.

It has been found that the administration of compounds having a high affinity for the serotonin 5-HT2c receptor site are able to phase shift an existing circadian rhythm by inhibiting melatonin production and causing delays in the onset of melatonin production for up to 3 nights following administration. In addition, it is known that core body temperature follows a circadian rhythm which can also be mediated by the administration of compounds, having a high affinity for a serotonin 5-HT2c receptor.

Among the compound or compounds having a high affinity for the 5-HT2c serotonin receptor are the following, although it should be stressed that the invention is not limited to these compounds:

(+/−)-1-(4-iodo-2,5-dimethoxy-phenyl)-2-aminopropane, (DOI); 1-(3-chlorophenyl)piperazine, (mCPP) and compounds which are metabolised to mCPP (desyrel, nefazodone and tradozone); 1-($\alpha,\alpha,\alpha$-trifluoro-m-tolyl)-piperazine, (TFMPP); (dl)-4-bromo-2,5-dimethoxyamphetamineHCl, (DOB); (dl)-2,5-dimethoxy-4-methylamphetamine HCl, (DOM); mesulergine; ritanserin; (clozapine; loxapine; R(+)-2-di-n-propylamino-8-hydroxy-1,2,3,4-tetrahydronapthalene, (SCH 23390); tiosperone; fluperlapine; rilapine; chlorpromazine; ketanserin; risperidone; cis-fluphenixol; quipazine; 6-chloro-2-(1-piperazinyl)pyrazine, (MK-212); spiperone; metergoline; methysergide; 6-methyl-1-(1-methylethyl)-ergoline-8-carboxylic acid (8$\beta$)-2-hydroxy-1-methylpropyl ester(Z)-2-butenedioate(1:1), (LY-53857); methiothepin; cyproheptadine; perenpirone; N-(1-methyl-5-indolyl-N-(3-pyridyl) urea, (SB-200646); pitozifen; 2-(2-dimethylaminoethylthio)-3-phenylquinoline, (ICI-169-369); lisuride; methergine; piremperone; ergometrine.

Preferably, the serotonin 5-HT2c receptor active compound is selected from the, group consisting of: DOI, mCPP, TFMPP, MK-212, and quipazine. More preferably still, the serotonin 5-HT2c receptor active compound is DOI.

Preferably, the serotonin 5-HT2c receptor active compound is administered at a concentration of 0.005–25 mg/kg of body weight.

In further aspects of the present invention it is possible to administer the therapeutically effective amount of a serotonin 5-HT2c receptor active compound or compounds in a timed manner, optionally in combination with melatonin to thereby further mediate an existing circadian rhythm, and in one form the invention may comprise a pharmaceutical package containing one or more therapeutically effective doses of a serotonin 5-HT2c receptor active compound or compounds, the package containing suitable indicia for calculating the dosage and timing of administration of the dosage to produce a selected mediation of the melatonin production cycle. The invention further comprises a method of treatment of the following conditions in mammals by administration of a therapeutically effective amount of a serotonin 5-HT2c receptor active compound; advanced phase sleep insomnia, delayed sleep phase insomnia, Seasonal Affective Disorder, Shift Work dysrhythmia, jet-lag, and the control of physiological systems which respond to light, and the control of seasonal breeding cycles of animals. Typically, the mediating effect on the circadian rhythms can be monitored experimentally in rats from an analysis of the output of the pineal gland via the urinary metabolite of melatonin, 6-sulphatoxymelatonin (aMT.6S) following drug treatment to provide information on the transmitters mediating the effects of light. Experimentally rats are maintained in metabolism cages and fed a high protein liquid diet to promote urine flow during the night. Urine produced is continuously pumped out of the urine collection vessels by a peristaltic pump and deposited in vials in a multi-channel fraction collector. Using this arrangement, hourly samples can be obtained non-invasively for more than four days. It can be demonstrated that light presented between 2–8 hours after dark onset (ie between ZT14 and ZT20) results in the acute suppression of aMT.6S excretion and causes the normal nocturnal increase to be delayed by several hours on subsequent nights. In subsequent studies, it has been found that light pulses of low intensity (2 lux) and short duration (1 minute) have this dual effect of acute suppression and phase delay when presented at CT18, that is 6 hours after subjective lights out in animals maintained in continuous darkness. The effects of administering an appropriate dose of an agonist compound having a high affinity for a serotonin 5-HT2c receptor provokes the equivalent of these light effects on pineal rhythmicity and causes a dose dependent acute suppression in melatonin production and a delay of up to several hours in the on set of production in subsequent nights. Thus, an existing circadian rhythm is delayed by the administration of the compounds to the extent of the delay in on set of production of melatonin. Alternatively, administration of a serotonin antagonist having a high affinity for the 5-HT2c receptor would block the phase advancing or delaying effects of a light pulse on the melatonin rhythm.

Additionally, by administering a plurality of doses of an appropriate 5-HT2c receptor active compound, or mixture of compounds at intervals, it is possible to induce a phase advance of a circadian rhythm. Thus, by administering repetitive doses, for example on two or more successive days just before subjective dawn (ie in the hours ZT21–ZT24) it will be possible to produce a phase advance of several hours. The administration of doses can be maintained until the desired mediated rhythm is established.

DETAILED DESCRIPTION OF THE PREFERRED EMBODIMENTS

Experimental Methods 1. 6-Sulphatoxymelatonin Rhythmicity

Male albino wistar rats (100 g, n=5–10) were housed in metabolism cages in lightproof environment chambers in 12 hours of light followed by 12 hours of darkness, designated 12L:12D. After 3–4 days acclimation to a liquid diet (Osmolite HN) hourly urine collections commenced. The general experimental design was:

Night 1: Control collection-lights remained off from lights out for the remainder of the experiment.

Night 2: Drug administration or light pulses administered at CT 18, i.e., 6 hours after the subjective lights out. Urine collections were maintained throughout the subjective night.

Nights 3 & 4: Urine collections continued to determine any entraining effects of the stimuli.

Melatonin production was monitored by the urinary excretion of 6-sulphatoxymelatonin (aMT.6S), determined by radioimmunoassay. The time of onset of metabolite excretion was defined as the time of day that the excretion rate exceeded 20 pmol/h.

Two lighting conditions were used to investigate the effects of drugs on SCN/pineal gland function; animals held in a light: dark cycle (L:D; Type VI method of Aschoff) and animals acutely transferred to continuous darkness (DD; Type II method of Aschoff) [Aschoff J. Response curves in circadian periodicity. In Aschoff J., ed. Circadian Clocks. Amsterdam: North Holland Publishing, 1965:95–111].

Core Body Temperature Rhythm Studies

Groups of 5 rats were implanted with temperature transmitters under 3% halothane/oxygen anaesthesia and kept in individual cages on a 12L: 12D photoperiod. Five days after implanting the transmitters, the lights were turned off at the normal time (ZT12) and remained off for 5 days. The animals were injected subcutaneously with either DOI (0.5 mg/kg) or saline vehicle at CT18 (ie 30 hours after last lights off). The temperature was sampled at 10 minute intervals. Five days after the drug treatment the animals were re-entrained to the LD cycle for 8 days and either exposed to a 5 minute/20 lux light pulse 30 hours after re-initiation of constant darkness or left untreated. To determine any delays in the temperature rhythm, the time of the day that the temperature dropped below the group daily mean (37.4° C.) was calculated and the mean delay±SEM determined.

Suprachiasmatic Nucleus c-Fos Immunocytochemistry

As a check on the specificity of the response (SCN versus direct pineal effects) experiments were also conducted to monitor c-Fos induction in the SCN in response to the treatments. Animals were sacrificed by decapitation 2 hours after treatments. Brains were removed immediately and fixed by immersion in a 4% solution of paraformaldehyde in 0.1 M buffer (pH 7.4) at room temperature. After approximately 30 hours in the fixative solution at room temperature, the brains were briefly rinsed in phosphate buffered saline (PBS) and 70 µm coronal sections were obtained on a microtome. Free floating sections were permeabilised in a 0.3% solution of Triton X-100 in PBS at 4° C. overnight. Endogenous peroxidase was inhibited for 3 minutes with a 7.5% solution of hydrogen peroxide and after washing, sections were incubated in a blocking solution of 0.5% bovine serum-albumin and 1% normal horse serum in 0.05M phosphate buffer (pH 7.2) for one hour and incubated for approximately 60 hours at 4° C. with 1:20,000 dilution of primary antibody against c-Fos. The immunopositive cells were quantified using a computerised image analysis system.

EXPERIMENTS

Serotonin Receptor Agonist Studies

To determine the effects of various serotonin agonists on melatonin rhythmicity, a selection of compounds was administered at CT18 to groups of five rats. For a comparison of responses to a light pulse a group of animals was exposed to 2 lux/1 minute. Urine was collected on the night before, the night of administration and for two nights afterwards. The compounds selected for investigation were as follows:

| | |
|---|---|
| 5-HT 1a agonist: | Buspirone (2 mg/kg) |
| 5-HT 1b agonist | CGS-12066a (2 mg/kg) |
| 5-HT 2a/2c agonists: | DOI (0.5 mg/kg); |
| | mCPP (2 mg/kg); |
| | TFMPP (2 mg/kg) |
| 5-HT 3 agonist: | Phenylbiguanide (10 mg/kg) |
| 5-HT 7 agonists: | (+)8-OH-DPAT (2 mg/kg), |
| | Clozapine (2 mg/kg) |

To determine the effects of serotonin agonists on the induction of c-Fos in the SCN, groups of, 4–8 rats were administered DOI, mCPP, TFMPP, buspirone or vehicle at CT18 and subsequently examined for immunocytochemistry.

Effects Of Serotonin Antagonists On DOI Responses

The effects of the serotonin antagonists ritanserin and ketanserin on the melatonin response to DOI was determined. Both drugs were administered in doses of 0.7, 0.28 and 0.07 µmole/kg, 30 minutes prior to DOI (1.4 µmole/kg; 0.5 mg/kg) at CT 18; In addition, ritanserin (6.3 µmole/kg) and ketanserin (18 µmole/kg) were administered 30 minutes prior to saline injection at CT 18. Both antagonists were dissolved in DMSO and injected in a volume of 200 µl.

To determine the effects of the antagonists on c-Fos induction in the SCN, ritanserin and ketanserin were injected in doses of 1.4, 0.7 and 0.14 µmole/kg at ZT 17.5. Followed after 30 minutes by DOI (1.4 µmole/kg) at ZT18. The response to ritanserin (6.3 µmole/kg) and ketanserin (18 µmole/kg) administered 30 minutes prior to saline injection at CT 18 was also determined.

Effect of Serotonin Antagonists on Light Responses

To determine the effects of the serotonin antagonist, metergoline (15 mg/kg), ritanserin (3 mg/kg) and LY-53,857 (3 mg/kg) on the melatonin response to a light pulse, the drugs were administered at CT17.5. At CT18, a 2 lux light pulse was given for one minute. Using similar methodology the effects on c-fos induction in the SCN were determined.

Excitatory Amino Acids (5R,10S)-(+)-5-methyl-10,11-dihydro-5H-dibenzo-[a,d] cyclo-hepten-5,10-imine (MK-801), a non-competitive antagonist of receptors of the excitatory amino acid N-methyl- D-aspartate (NDMA) was used to investigate the role of NDMA receptors in mediating the effects of light on melatonin production in the rat. MK-801(3 mg/kg) or DMSO vehicle were injected 30 minutes prior to DOI (0.5 mg/kg, 1.4 µmole/kg) administration at CT18.

RESULTS

Figure 1:
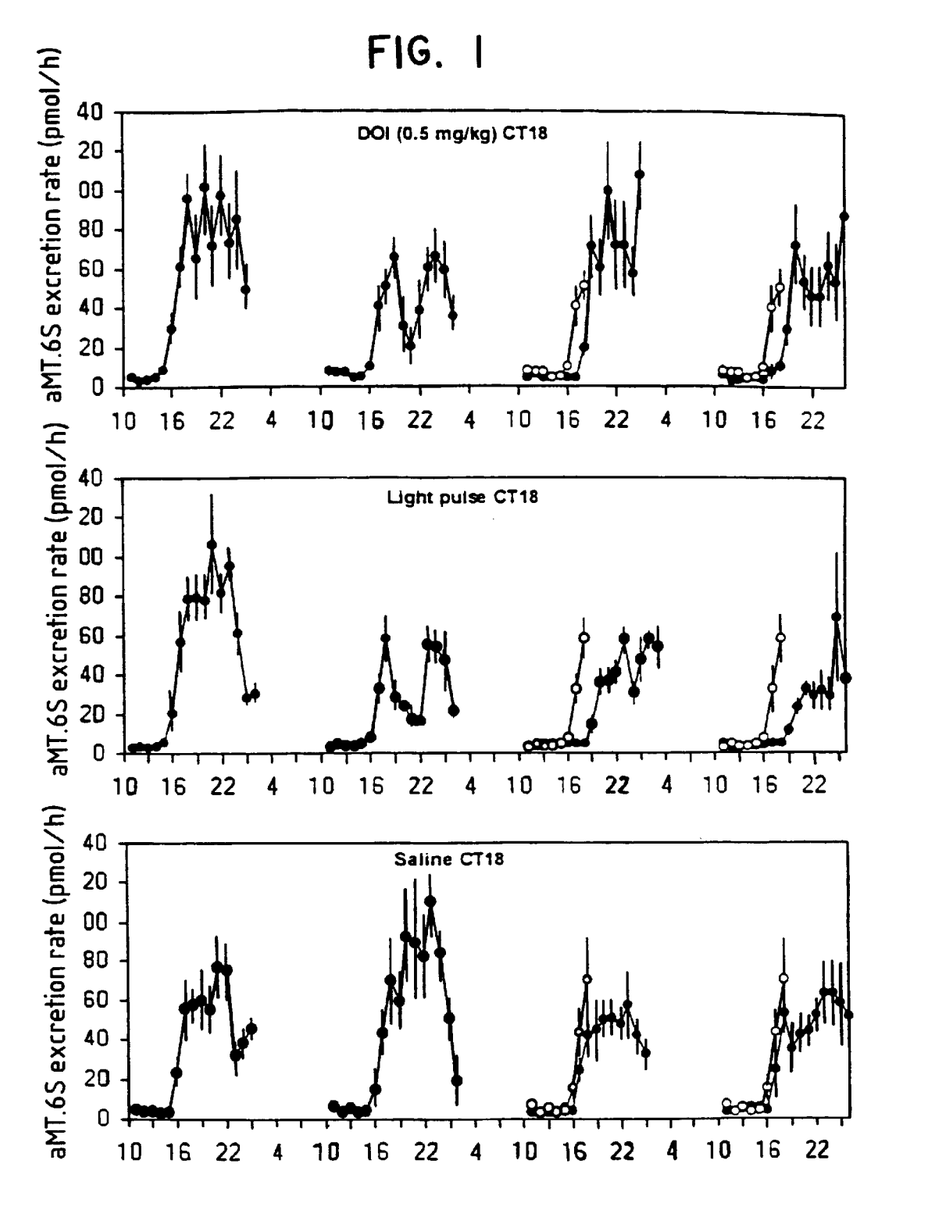
FIG. 1 is three graphical representations of the effects of serotonin antagonists on DOI responses, light responses, and saline responses, as measured in aMT.6S excretion over circadian time, in experiments involving rats.

FIG. 1 illustrates the effects of top panel DOI (0.5 mg/kg; 1.4 µmole/kg), middle panel a 2 lux/1 minute light pulse and bottom panel saline administration at CT18 (6 hours after subjective light off), on the pattern of aMT.6S excretion in rats in individual experiments. The filled symbols (●—●) show the excretion rate across the 4 nights of the experiment. The open symbols (○—○) represent the excretion rate from CT11–CT18 on night 2 replotted on nights 3 and 4 to emphasise any changes in the onset of excretion provoked by the treatments. Data are the mean ±SEM (pmol/h, n=5). The abscissa shows the time as circadian time where CT12 represents the time of subjective lights off in continuous darkness. For comparison, the response to exposure to 2 lux light for 1 minute and saline injection are also shown. DOI caused an acute decrease in melatonin metabolite excretion immediately following injection. On the subsequent two nights, the increase in aMT.6S excretion was delayed by one to two hours, reflecting a permanent alteration in the rhythmic output from the SCN to the pineal gland. A light pulse applied at CT18 resulted qualitatively and quantitatively similar responses.

Figure 2:
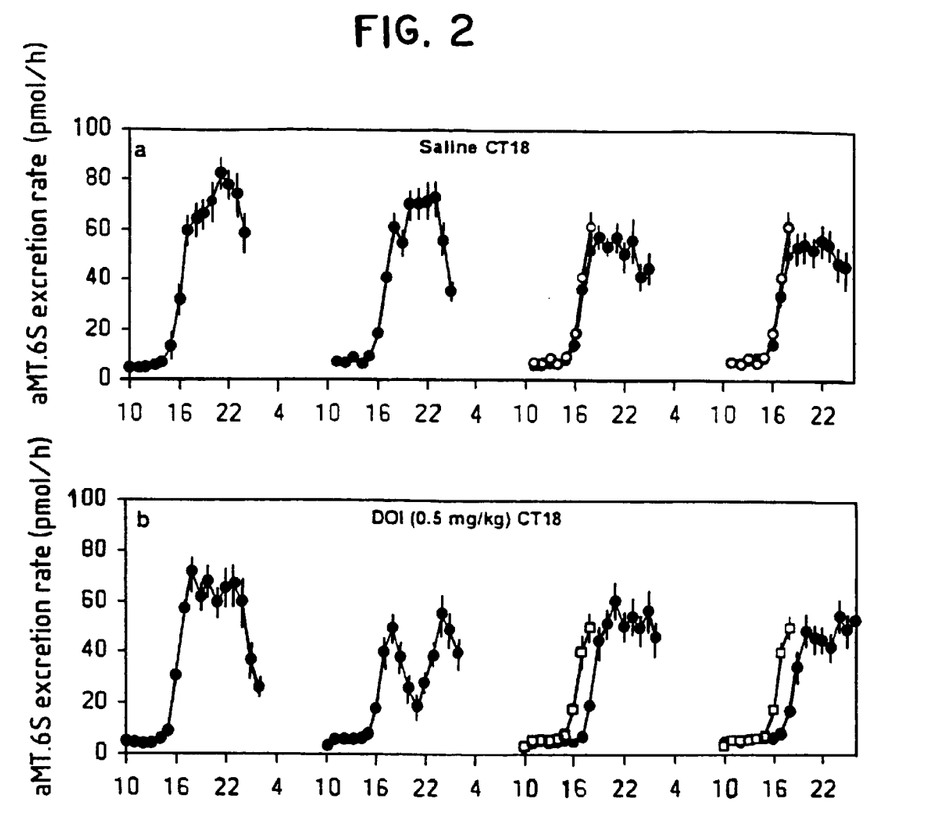
FIG. 2a is a graphical representation of the effects of vehicle administration on the pattern of aMT.6S excretion over circadian time in experiments involving rats.
FIG. 2b is a graphical representation of the effects of DOI administration on the pattern of aMT.6S excretion over circadia time in experiments involving rats.

FIG. 2 illustrates the effects of (a) vehicle or (b) DOI (0.5 mg/kg; 1.4 $\mu$mole/kg) administration at CT18 on the pattern of aMT.6S excretion in rats. The data are the mean±SEM of 35 vehicle treated animals in seven independent experiments and 30 DOI treated animals from six independent experiments. The filled symbols (●—●) show the excretion rate across the 4 nights of the experiment (the gaps are times when aMT.6S excretion is low and/or urine flow irregular). The open symbols (○—○) represent the excretion rate from CT11–CT18 on night 2 replotted on nights 3 and 4 to emphasise any changes in the onset of excretion provoked by the treatments. The abscissa shows the time as circadian time where CT12 represents the time of subjective lights off in continuous darkness.

Figure 3:
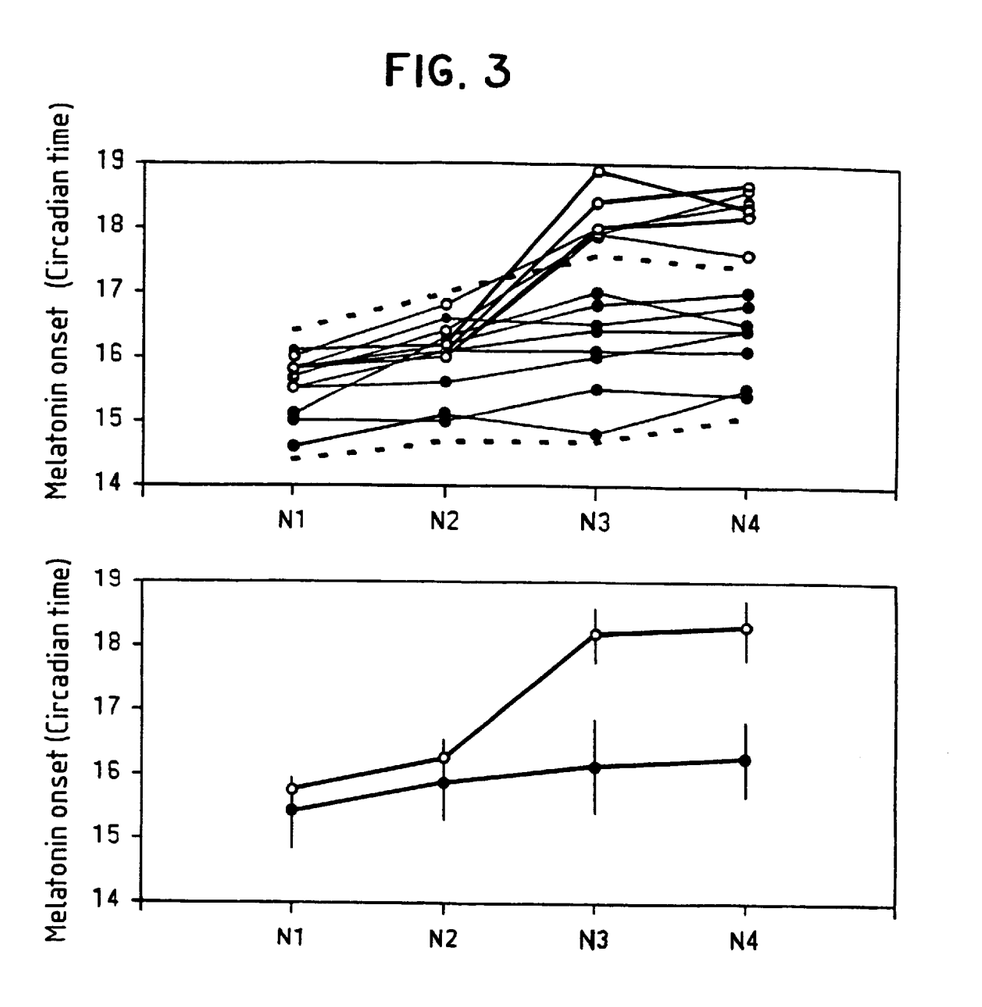
FIG. 3 is two graphical representations of the delay in onset of aMT.6S excretion in experiments involving vehicular saline treatment and DOI treatment.

FIG. 3 Demonstrates the times of onset of aMT.6S excretion in 7 experiments involving vehicle treatment at CT18 and 6 experiments involving DOI treatment. The top panel shows the mean times of onset for each experiment (five animals per experiment) on the four nights of sampling. The vehicle experiments are indicated by (●—●) and the DOI experiments by (○—○). The broken lines trace two standard deviations from the overall means of the control experiments. The bottom panel shows the mean±SEM onsets for the seven vehicle experiments and the six DOI experiments.

Figure 4:
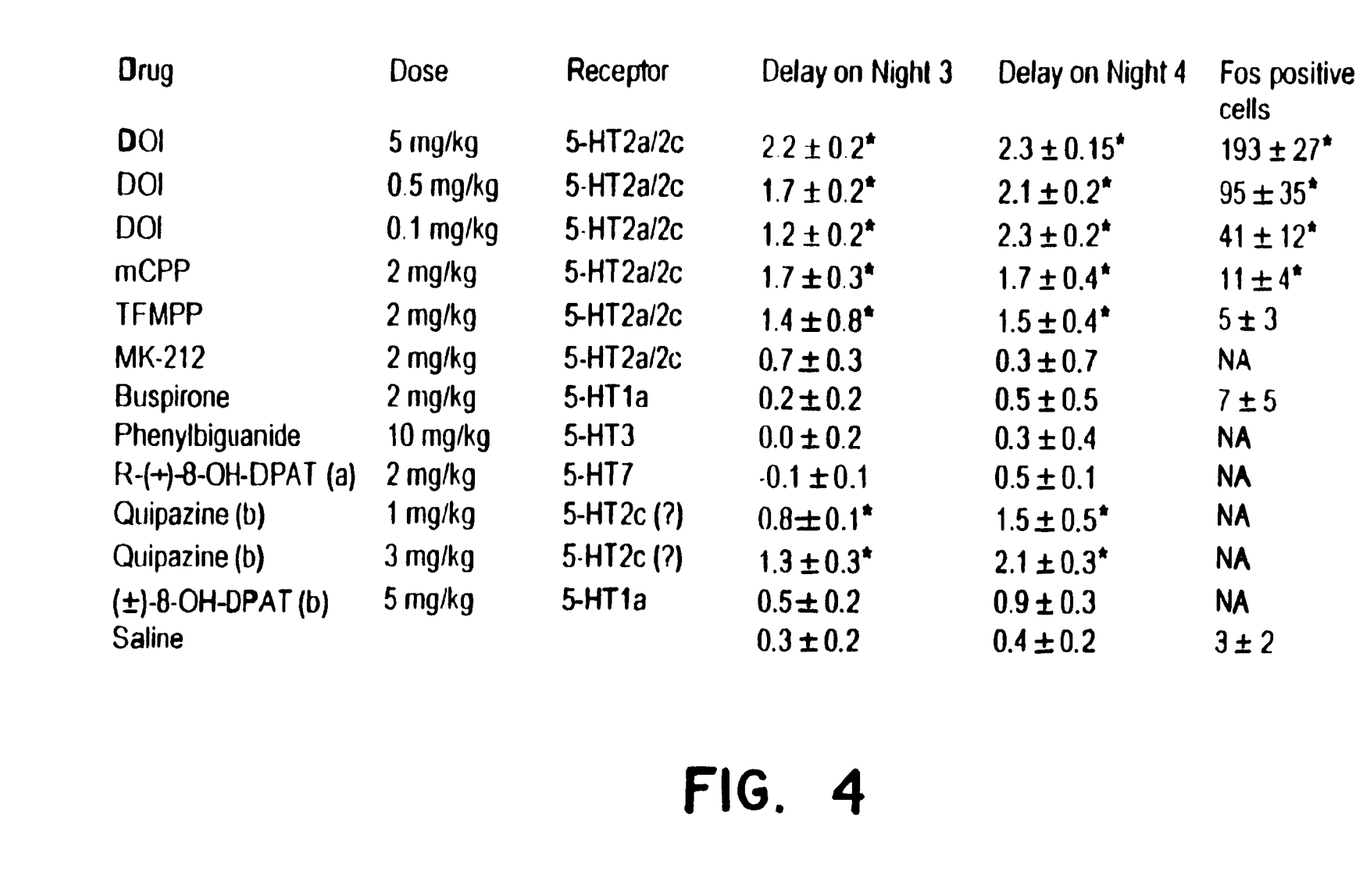
FIG. 4 is a table showing the effects of various serotonergic drugs on the onset of melatonin production and the appearance of c-Fos positive cells in subject rat SCN.

FIG. 4 illustrates in tabular form the effects of various serotonergic drugs, administered at CT18 on the onset of melatonin production and the appearance of c-Fos positive cells in the rat SCN. The data show the mean±SEM (hours, n=5) delaying the onset of aMT.6S excretion on the two nights after administration of the various serotonin agonists sub cutaneously at CT18.

The asterisk indicates a significant delay in the onset compared to night 2. In the case of the c-Fos labelled cells the mean number of positive cells±SEM per unilateral SCN are shown for 4–8 animals in each group. NA indicates the effects of the drug were not tested. The asterisk indicates significantly different from the control (vehicle) treated animals ($P<0.05$). Administration of compounds active as agonists for the 5-HT2c receptor resulted in c-Fos appearance in the ventrolateral division of the SCN. By comparison, administration of compounds active at alternative receptor sites did not produce this effect. The results that were qualitatively similar to those found for melatonin rhythm.

Figure 5A:
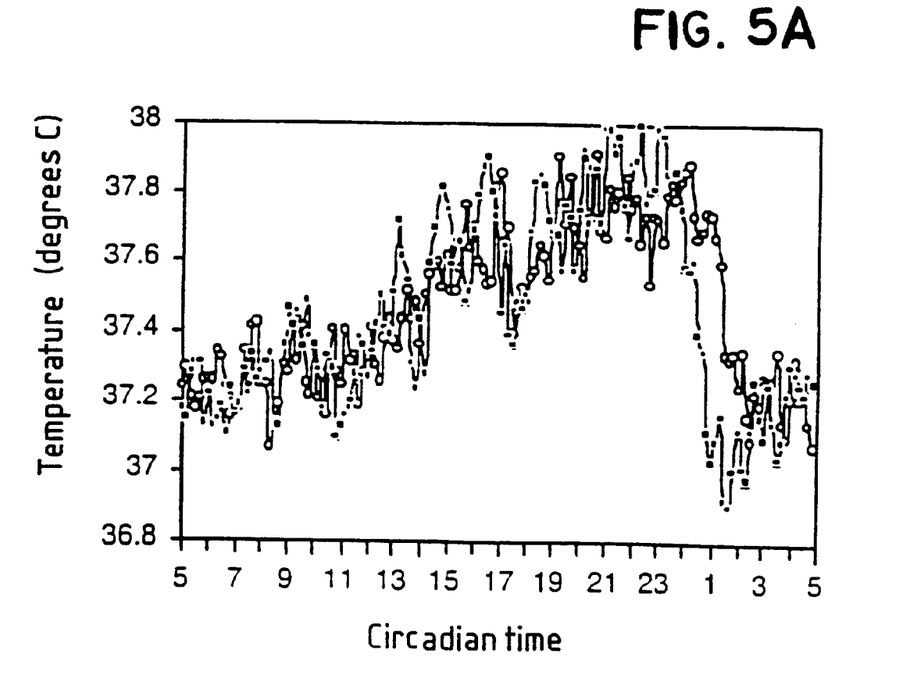
FIG. 5A is a graphical representation of the effects of DOI administration, as compared with saline administration, on core body temperature rhythm in experiments involving rats.
Figure 5B:
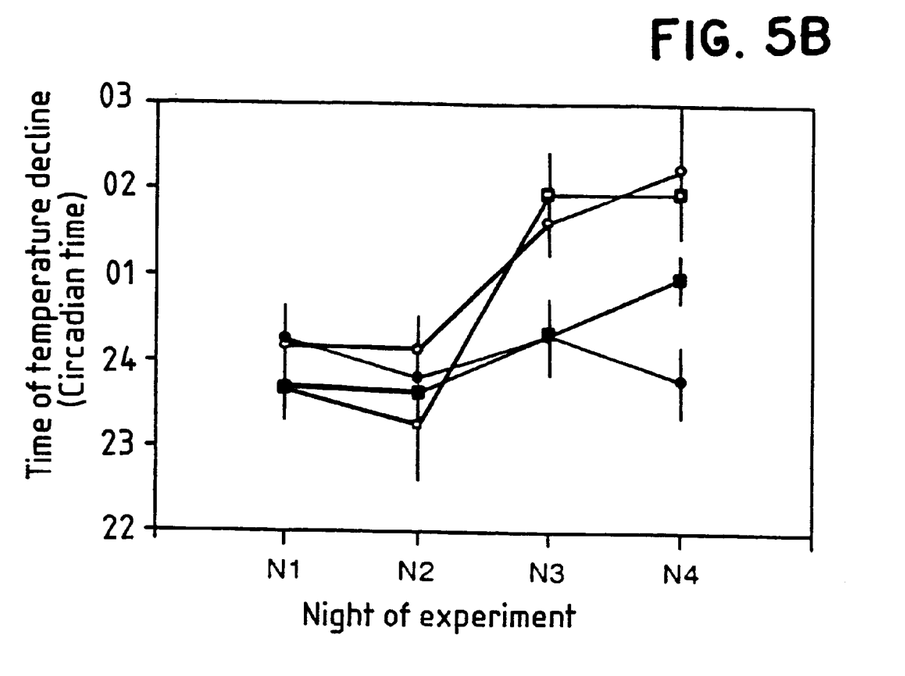
FIG. 5B is a graphical representation of the effects of DOI administration, as compared with saline administration, on the rate of morning temperature decline, both compared with the rate of morning temperature decline in response to a low-level light pulse.

FIG. 5 Demonstrates the effect of DOI (0.5 mg/kg) administration at CT18 on the core body temperature rhythm in rats. Panel A shows the mean temperature of 2 groups of 5 rats on the night after they had been injected with saline (■—■) or DOI (○—○). Note the delayed decline in temperature at around CT0 in the drug treated group. The results are the mean temperatures determined at 10 minute intervals (the SEM have been omitted for clarity). Panel B shows the effect of DOI (○—○) or saline (●—●) on the timing of the temperature decline compared to the response to a 5min/20 lux light pulse at CT18 (□—□) or no treatment (■—■) on the morning before (N1), the morning directly after (N2) and 2 subsequent mornings (N3 and N4). Both DOI and light significantly delayed the morning decline in body temperature.

Figure 6:
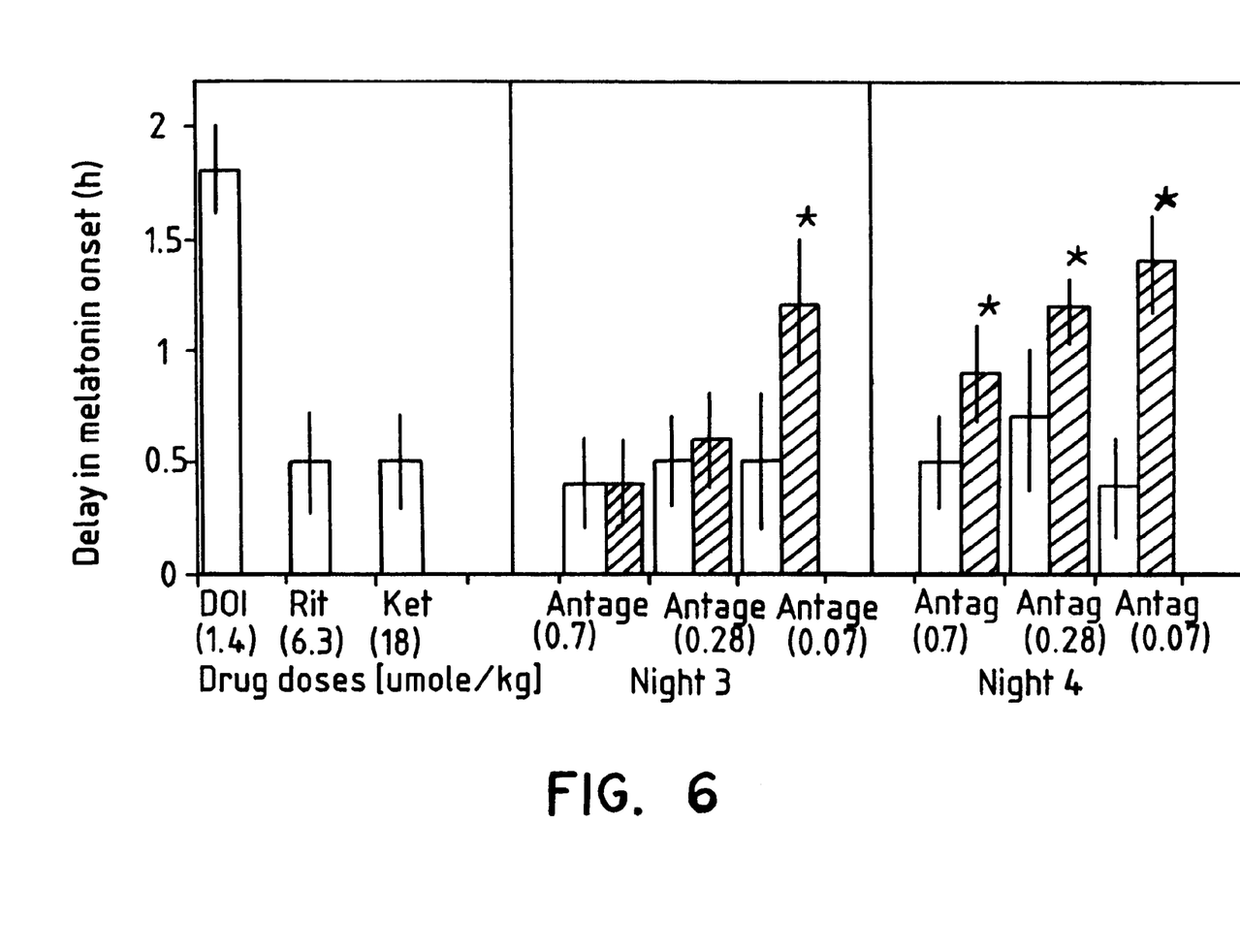
FIG. 6 is a graphical representation of the effects of pre-treatment with serotonin antagonists ritanserin and ketanserin on the delay in the onset of melatonin production provided by DOI administration.

FIG. 6 The effects of pre-treatment with serotonin antagonists ritanserin and ketanserin on the delay in the onset of melatonin production provoked by DOI administration at CT18. The data are the mean (±SEM) delays in onset (hours; n=5). The bars in the left panel show the effects of DOI, ritanserin and ketanserin alone at CT18 on the onset of melatonin production on the night after drug administration. The centre panel shows the effects of ritanserin (open bars) and ketanserin (black bars) pre-treatment 30 minutes before the administration of DOI (1.4 $\mu$mole/kg) at CT18 on the night after drug treatment. The doses of the antagonist drugs are shown in brackets. The right panel shows the effects of pre-treatment with ritanserin (open bars) and ketanserin (black bars) 30 minutes before the administration of DOI (1.4 $\mu$mole/kg) at CT18 on the second night after drug treatment. The asterisk indicates a significant difference ($P<0.01$) between ritanserin and ketanserin in treated groups.

Figure 7:
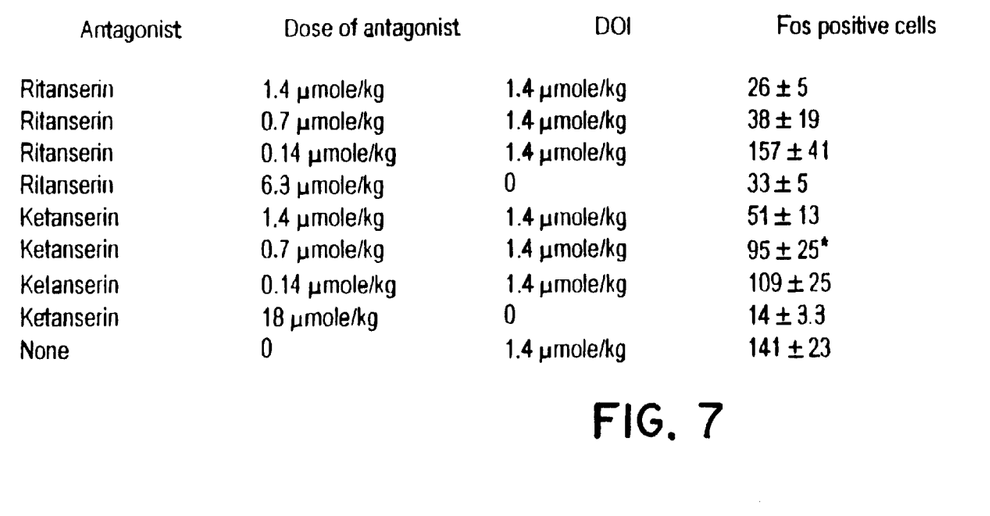
FIG. 7 is a table showing the effects of pre-treatment with serotonin antagonists ritanserin and ketanserin on DOI induced c-Fos in subject rat SCN.

FIG. 7 gives details in tabular form of the effects of pre-treatment with the serotonin antagonists ritanserin and ketanserin on DOI induced c-Fos in the rat SCN. The mean number of c-Fos labelled cells (±SEM) per unilateral SCN are shown for 4–8 animals in each group and the asterisk indicates that at the ketanserin dose of 0.7 $\mu$mole/kg the number of cells positive for c-Fos were significantly greater ($P<0.05$) than those observed following ritanserin 0.7 $\mu$mole/kg but not significantly different from the vehicle control.

It can be seen that at a dose of 0.07 $\mu$mole/kg ritanserin inhibits the DOI induced phase delay in melatonin production, whereas ketanserin is ineffective at this dose. It is known that ritanserin has a 10 fold higher affinity for 5-HT2c receptors than ketanserin, providing strong evidence that the action of DOI occurs through 5-HT2c receptors.

Figure 8:
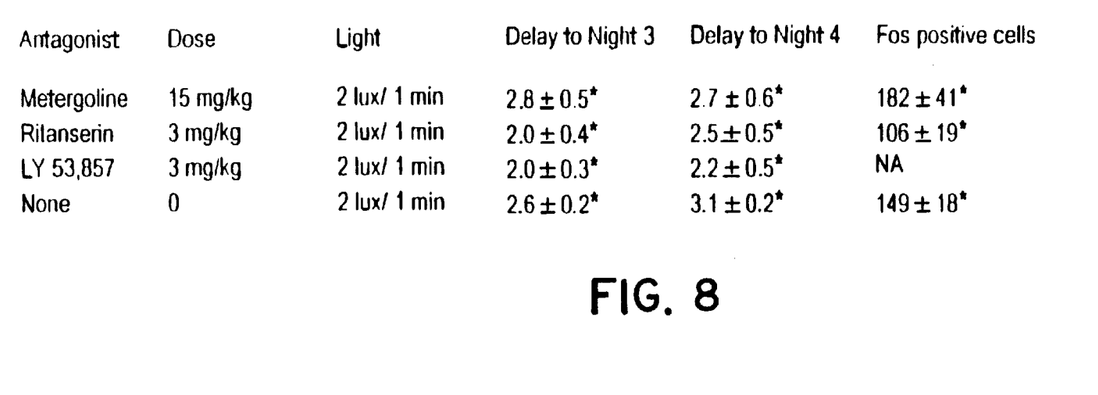
FIG. 8 is a table showing the effects of pre-treatment with serotonin antagonists metergoline and ritanserin on the delayed onset of melatonin production and the appearance of c-Fos in subject rat SCN.

FIG. 8 Shows in tabular form the effects of pre-treatment with the serotonin antagonists metergoline and ritanserin on the delayed onset of melatonin production and the appearance of c-Fos positive cells in the SCN induced by a 2 lux/1 minute light pulse at CT18. The data show the mean±SEM (hours, n=5) delay in the onset of aMT.6S excretion on the two nights after administration of the various drugs. The antagonists were administered at CT17.5 and the light pulse given at CT18. The delays were calculated as the difference from the onsets on the second night of the experiment. The asterisk indicates the delays were significant ($P<0.01$). In the case of the c-Fos labelled cells the mean number of positive cells (±SEM) per unilateral SCN are shown for 4–8 animals in each group. The asterisk indicates that the number of Fos positive cells was significantly higher than dark or drug-only controls ($P<0.05$). There was no significant difference between the 3 groups. Again, ritanserin has a greater effect than ketanserin on the inhibition of the increase in appearance c-Fos that results from the administration of a compound having a high affinity for the 5-HT2c receptor site.

Figure 9:
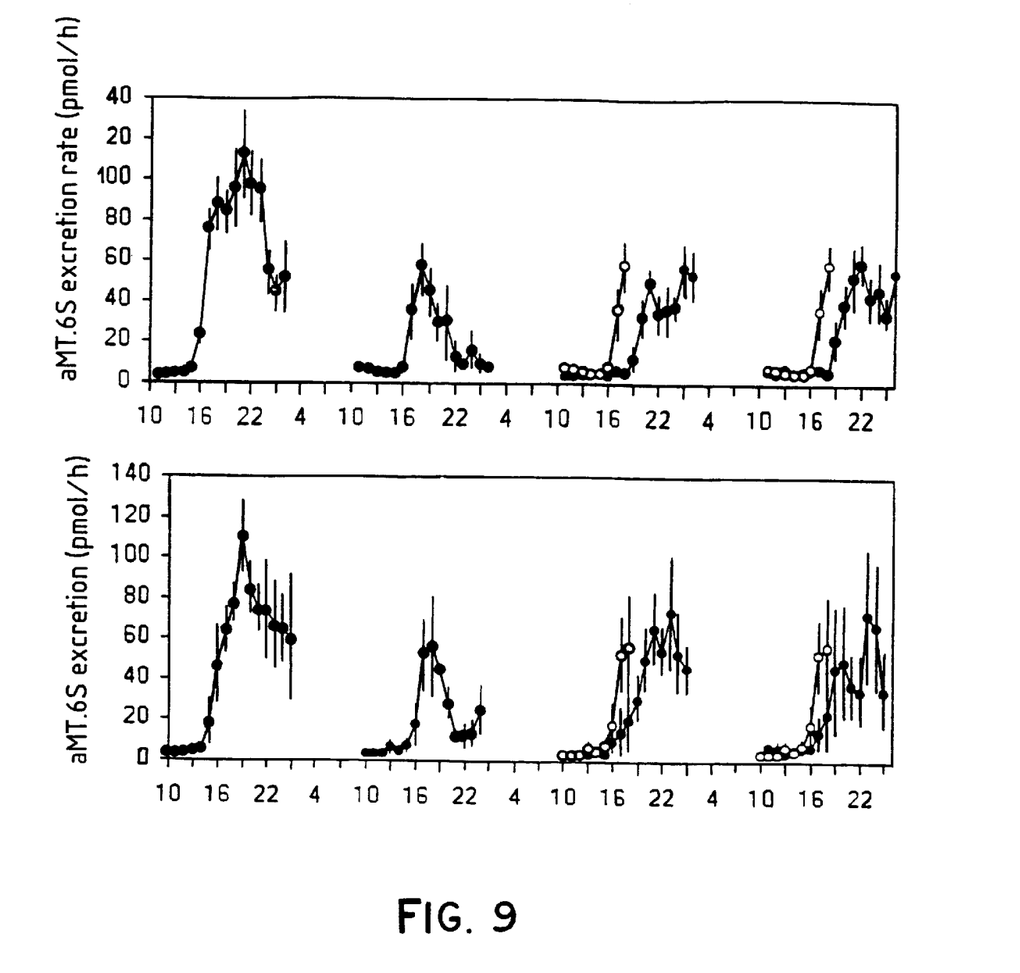
FIG. 9 is two graphical representations of the delay in onset of aMT.6S secretion as an effect of pre-treatment with the serotonin antagonists metergoline and ritanserin on 6-sulphatoxymelatonin rhythmicity.

FIG. 9 represents the effect of pre-treatment at CT17.5 with the serotonin antagonists metergoline (15 mg/kg) and ritanserin (3 mg/kg) before exposure to light (2 lux/1 minute) at CT18 on 6-sulphatoxymelatonin rhythmicity. Data are the mean±SEM (pmol/h, n=5). The aMT.6S excretion rate between CT11 and CT18 on night 2 is replotted (○—○) on night 3 and night 4 to highlight the failure of the antagonists to block the phase delay in the onset induced by the light pulse. The data show the mean±SEM (hours, n=5) delay in the onset of aMT.6S excretion on the two nights after administration of the various drugs. The antagonists were administered at CT17.5.

Figure 10:
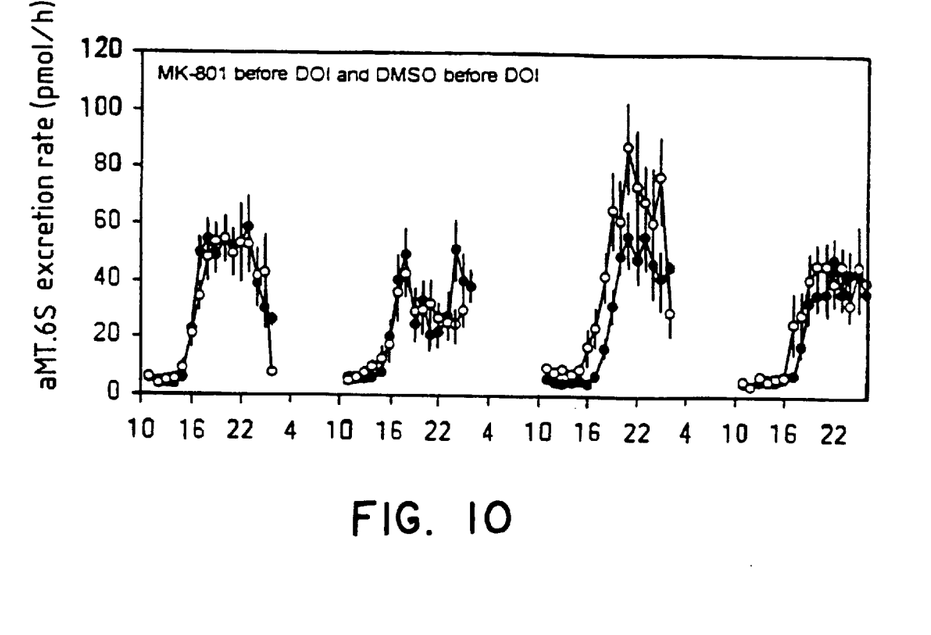
FIG. 10 is a graphical representation of the effects of MK-801 and DMSO vehicle injected 30 minutes prior to DOI administration on the pattern of aMT.6S excretion in rats.

FIG. 10 shows the effects of MK-801 (3 mg/kg) or DMSO vehicle injected 30 minutes prior to DOI (0.5 mg/kg; 1.4 μmole/kg) administration at CT18 on the pattern of aMT.6S excretion in rats. The data are the mean±SEM of 10 animals in 2 independent experiments. The filled symbols (●—●) show the excretion rate across the 4 nights for the DMSO vehicle/DOI treated animals (the gaps are times when aMT.6S excretion is low and/or urine flow irregular). The open symbols (○—○) show the excretion: rate across the 4 nights for the MK-801/DOI treated animals The abscissa shows the time as circadian time where CT12 represents the time of subjective lights off in continuous darkness.

Figure 11:
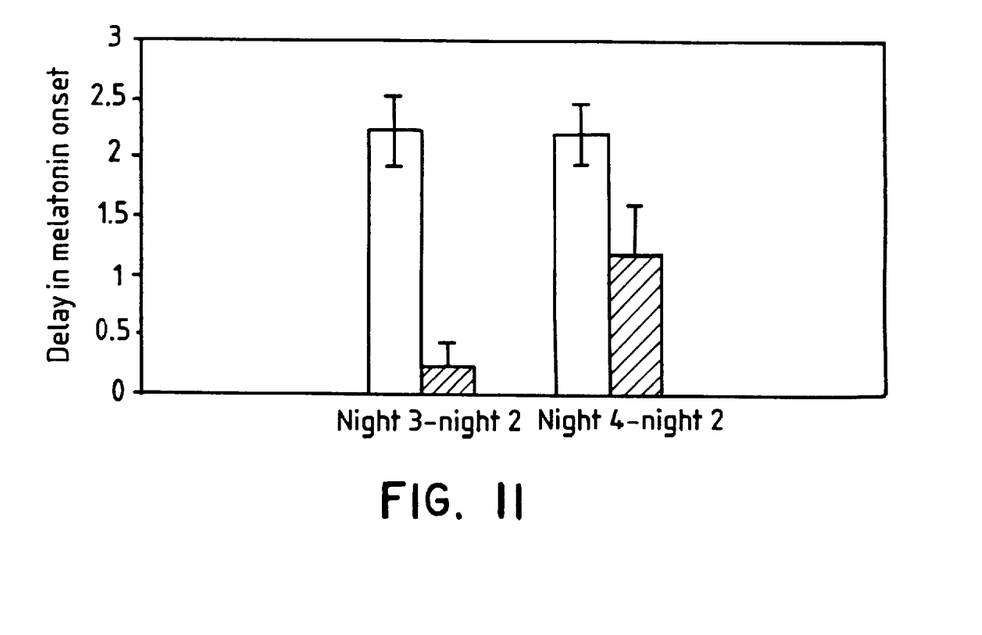
FIG. 11 is a graphical representation of the effect of prior MK-801 pre-treatment on the delay in melatonin onset induced by DOI.

FIG. 11 demonstrates the effect of prior MK-801 pretreatment on the delay in melatonin onset induced by DOI. DMSO vehicle (empty boxes) or MK-801 (3 mg/kg, filled boxes) were injected 30 minutes prior to DOI (0.5 mg/kg; 1.4 μmole/kg) administration at CT18. The onset of melatonin production were calculated and delays expressed in relation to the onset on night 2. The data are the mean±SEM of 10 animals in 2 independent experiments.

I claim:

1. A method of mediating the effects of circadian rhythms in mammals comprising the step of administering a therapeutically effective amount of at least one compound having a high affinity and selectivity for a serotonin $5\text{-HT}_{2c}$ receptor.

2. The method of mediating the effects of circadian rhythms in mammals according to claim 1, wherein timing of administration of the compound is pre-determined to coincide with an appropriate phase on an existing circadian rhythm to produce a selected mediation of the cycle.

3. The method of mediating the effects of circadian rhythms in mammals according to claim 2, wherein said mediation comprises a phase shift of an existing melatonin production circadian rhythm resulting in an inhibition of melatonin production following administration of the compound and subsequent delays in the onset of melatonin production up to 72 hours following administration.

4. The method of mediating the effects of circadian rhythms in mammals according to claim 2, wherein said mediation comprises inducing a phase advance in melatonin production by administering a plurality of doses of the compound on successive days to establish a mediated circadian rhythm.

5. The method of mediating the effects of circadian rhythms in mammals according to claim 2, wherein said mediation comprises mediation of the core body temperature circadian rhythm.

6. The method of mediating the effects of circadian rhythms in mammals according to claim 1, wherein said compound is selected from the group consisting of: (+/−)-1-(4-iodo-2,5-dimethoxy-phenyl)-2-aminopropane; 1-(3-chlorophenyl)piperazine; desyrel; nefazodone; tradozone; 1-($\alpha,\alpha,\alpha$-trifluoro-m-tolyl)-piperazine; (dl)-4-bromo-2,5-dimethoxyamphetamineHCl; (dl)-2,5-dimethoxy-4-methylamphetamine HCl; quipazine; and 6-chloro-2-(1-piperazinyl)pyrazine.

7. The method of mediating the effects of circadian rhythms in mammals according to claim 1, wherein said compound is (+/−)-1-(4-iodo-2,5-dimethoxy-phenyl)-2-aminopropane.

8. The method of mediating the effects of circadian rhythms in mammals according to claim 1, wherein said compound is administered at a concentration of 0.005–25 mg/kg.

9. The method of mediating the effects of circadian rhythms in mammals according to claim 1, wherein said therapeutically effective amount of the compound is administered in a predetermined dosage sequence with melatonin.

10. A method of treatment in mammals of the conditions of advanced phase sleep insomnia, delayed sleep phase insomnia, Seasonal Affective Disorder, Shift Work dysrhythmia, jet-lag, the control of physiological systems which respond to light, and the control of seasonal breeding cycles of animals, comprising the step of administering a therapeutically effective amount of at least one compound having a high affinity and selectivity for a serotonin 5-HT2c receptor.

11. A method of mediating the effects of circadian rhythms in mammals according to claim 1, wherein said compound is a serotonin 5-HT2c receptor agonist.

12. The method of treatment according to claim 10, wherein the compound is a serotonin 5-HT2c receptor agonist.

* * * * *

UNITED STATES PATENT AND TRADEMARK OFFICE
CERTIFICATE OF CORRECTION

PATENT NO.   : 6,403,651 B1
DATED        : June 11, 2002
INVENTOR(S)  : David Kennaway It is certified that error appears in the above-identified patent and that said Letters Patent is hereby corrected as shown below:

<u>Column 10,</u>
Line 24, "0.005" should be -- .005 --.

Signed and Sealed this

Twenty-second Day of April, 2003

JAMES E. ROGAN
*Director of the United States Patent and Trademark Office*